US00PP26616P2

(12) United States Plant Patent
Wood

(10) Patent No.: US PP26,616 P2
(45) Date of Patent: Apr. 19, 2016

(54) ***CYTISUS* PLANT NAMED 'SMSCGF'**

(50) Latin Name: *Cytisus scoparius*
Varietal Denomination: SMSCGF

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 23 days.

(21) Appl. No.: 14/121,369

(22) Filed: Aug. 26, 2014

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

*Primary Examiner* — Kent L Bell
(74) *Attorney, Agent, or Firm* — C. A. Whealy

(57) ABSTRACT

A new and distinct cultivar of *Cytisus* plant named 'SMSCGF', characterized by its compact, low mounding and arching plant habit; vigorous growth habit; freely branching habit; full and dense plants; freely flowering habit; large bright yellow-colored flowers; and good garden performance.

2 Drawing Sheets

Botanical designation: *Cytisus scoparius*.
Cultivar denomination: 'SMSCGF'.

BACKGROUND OF THE INVENTION

The present invention relates to a new and distinct cultivar of *Cytisus* plant, botanically known as *Cytisus scoparius*, commonly referred to as Scotch Broom and hereinafter referred to by the name 'SMSCGF'.

The new *Cytisus* plant is a product of a planned breeding program conducted by the Inventor in Grand Haven, Mich. The objective of the breeding program is to create new mounding *Cytisus* plants with attractive flower form and color.

The new *Cytisus* plant originated from an open-pollination in 2009 in Grand Haven, Mich. of an unnamed selection of *Cytisus scoparius*, not patented, as the female, or seed, parent with an unknown selection of *Cytisus scoparius* as the male, or pollen, parent. The new *Cytisus* plant was discovered and selected by the Inventor as a simple flowering plant within the progeny of the stated open-pollination in a controlled environment in Grand Haven, Mich. in April, 2011.

Asexual reproduction of the new *Cytisus* plant by softwood cuttings in a controlled environment in Grand Haven, Mich. since June, 2011 has shown that the unique features of this new *Cytisus* plant are stable and reproduced true to type in successive generations.

SUMMARY OF THE INVENTION

Plants of the new *Cytisus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMSCGF'.

These characteristics in combination distinguish 'SMSCGF' as a new and distinct *Cytisus* plant:

1. Compact, low mounding and arching plant habit.
2. Vigorous growth habit.
3. Freely branching habit; full and dense plants.
4. Freely flowering habit.
5. Large bright yellow-colored flowers.
6. Good garden performance.

Plants of the new *Cytisus* can be compared to plants of the female parent selection. Plants of the new *Cytisus* differ primarily from plants of the female parent selection in the following characteristics:

1. Plants of the new *Cytisus* are more compact than plants of the female parent selection.
2. Plants of the new *Cytisus* are low mounding and arching in plant habit whereas plants of the female parent selection are upright in plant habit.
3. Plants of the new *Cytisus* have larger flowers than plants of the female parent selection.

Plants of the new *Cytisus* can be compared to plants of *Cytisus scoparius* 'Moonlight', not patented. In side-by-side comparisons conducted in Grand Haven, Mich., plants of the new *Cytisus* differed from plants of 'Moonlight' in the following characteristics:

1. Plants of the new *Cytisus* were more compact than plants of 'Moonlight'.
2. Plants of the new *Cytisus* were low mounding and arching in plant habit whereas plants of 'Moonlight' were more upright and somewhat arching in plant habit.
3. Plants of the new *Cytisus* had larger flowers than plants of 'Moonlight'.
4. Flowers of plants of the new *Cytisus* were darker yellow in color than flowers of plants of 'Moonlight'.

BRIEF DESCRIPTION OF THE PHOTOGRAPHS

The accompanying colored photographs illustrate the overall appearance of the new *Cytisus* plant showing the colors as true as it is reasonably possible to obtain in colored reproductions of this type. Colors in the photographs may differ slightly from the color values cited in the detailed botanical description which accurately describe the colors of the new *Cytisus* plant.

The photograph on the first sheet comprises a side perspective view of a typical flowering plant of 'SMSCGF' grown in a container.

The photograph on the second sheet is a close-up view of a typical flowering plant of 'SMSCGF '.

DETAILED BOTANICAL DESCRIPTION

The aforementioned photographs and following observations and measurements describe plants grown during the spring and summer in an outdoor nursery in Grand Haven, Mich. and under cultural practices typical of commercial *Cytisus* production. Plants were two years old when the photographs and description were taken. In the following description, color references are made to The Royal Horticultural Society Colour Chart, 1995 Edition, except where general terms of ordinary dictionary significance are used.

Botanical classification: *Cytisus scoparius* 'SMSCGF'.

Parentage:

*Female, or seed, parent*.—Unnamed selection of *Cytisus scoparius*, not patented.

*Male, or pollen, parent*.—Unknown selection of *Cytisus scoparius*, not patented.

Propagation:

*Type*.—By softwood cuttings.

*Time to initiate roots, summer*.—About 30 days at temperatures about 20° C.

*Time to produce a rooted young plant, summer*.—About six months at temperatures about 20° C.

*Root description*.—Fine to medium in thickness, somewhat fibrous and fleshy; white in color.

*Rooting habit*.—Freely branching; dense.

Plant description:

*Plant form and habit*.—Perennial deciduous shrub; compact, low mounding and arching plant habit; freely branching habit with numerous lateral branches developing per plant; full and dense plant habit; vigorous growth habit.

*Plant height*.—About 14 cm.

*Plant diameter*.—About 40 cm.

Lateral branch description:

*Length*.—About 30 cm.

*Diameter*.—About 3 mm.

*Internode length*.—About 6 mm.

*Strength*.—Strong.

*Aspect*.—Horizontal to downwardly arching.

*Texture*.—Smooth, glabrous.

*Color, developing*.—Close to 137A.

*Color, developed*.—Close to 147B.

Leaf description:

*Arrangement*.—Alternate; leaves simple or compound with three leaflets per leaf.

*Simple leaf length*.—About 1.1 cm.

*Simple leaf width*.—About 3 mm.

*Compound leaf length*.—About 2.2 cm.

*Compound leaf width*.—About 1.5 cm.

*Leaflet length*.—About 7 mm.

*Leaflet width*.—About 3 mm to 4 mm.

*Simple leaf and leaflet shape*.—Lanceolate to oblanceolate.

*Simple leaf and leaflet apex*.—Acute.

*Simple leaf and leaflet base*.—Cuneate to attenuate.

*Simple leaf and leaflet margin*.—Entire.

*Simple leaf and leaflet texture, upper and lower surfaces*.—Slightly pubescent.

*Simple leaf and leaflet venation pattern*.—Pinnate.

*Simple leaf and leaflet color*.—Developing leaves, upper and lower surfaces: Close to 137A. Fully expanded leaves, upper and lower surfaces: Close to 137B; venation, close to 137B.

*Petioles*.—Length: About 1 cm. Diameter: About 1.5 mm. Color, upper and lower surfaces: Close to 137B.

Flower description:

*Flower arrangement and habit*.—Single axillary papilionaceous flowers; flowers face outward to drooping; freely flowering habit with about 300 flowers developing per plant.

*Natural flowering season*.—Plants flower continuously during the spring in Michigan.

*Flower longevity on the plant*.—Flowers last about two to three weeks; flowers not persistent.

*Fragrance*.—None detected.

*Flowers*.—Diameter: About 2.1 cm. Depth (height): About 3 cm.

*Flower buds*.—Length: About 1.9 cm. Diameter: About 3.5 cm. Shape: Pea-like. Color: Close to 9A.

*Corolla*.—Quantity and arrangement: Single whorl of five petals; one petal larger than the other four petals. Petal length, largest petal: About 2 cm. Petal length, smaller four petals: About 2 cm. Petal width, largest petal: About 1.7 cm. Petal width, smaller four petals: About 1 cm. Petal lobe shape, all petals: Oblong. Petal lobe apex, all petals: Obtuse. Petal lobe margin, all petals: Entire. Petal texture, all petals, upper and lower surfaces: Smooth, glabrous; silky. Color, all petals: When opening and fully opened, upper surface: Close to 13A. When opening and fully opened, lower surface: Close to 13A.

*Calyx*.—Quantity and arrangement: Two, opposite. Sepal length: About 3 mm. Sepal width: About 1.5 mm. Sepal shape: Lanceolate to oblong. Sepal apex: Acute. Sepal base: Fused. Sepal margin: Entire. Sepal texture, upper and lower surfaces: Smooth, glabrous. Sepal color, upper and lower surfaces: Close to 143C.

*Peduncles*.—Length: About 1 cm. Diameter: About 1 mm. Strength: Strong; flexible. Aspect: About 30° from lateral branch axis. Texture: Smooth, glabrous. Color: Close to 143C.

*Reproductive organs*.—Stamens: Quantity: Numerous, fused; monodelphous. Anther size: About 0.5 mm by 2 mm. Anther shape: Oblong. Anther color: Close to 13A. Pollen amount: Scarce. Pollen color: Close to 13A. Pistils: Quantity: One per flower. Pistil length: About 3 cm. Stigma shape: Round. Stigma color: Close to 12B. Style length: About 2.5 mm. Style color: Close to 12B. Ovary color: Close to 191C. Seeds and fruits: Seed and fruit development have not been observed on plants of the new *Cytisus*.

Garden performance: Plants of the new *Cytisus* have been observed have good garden performance as exhibited by its tolerance to rain and wind. Plants of the new *Cytisus* have been observed to tolerate temperatures ranging from about −32° C. to about 36° C.

Pathogen & pest resistance: Plants of the new *Cytisus* have not been observed to be resistant to pathogens and pests common to *Cytisus* plants.

It is claimed:

1. A new and distinct *Cytisus* plant named 'SMSCGF' as illustrated and described.

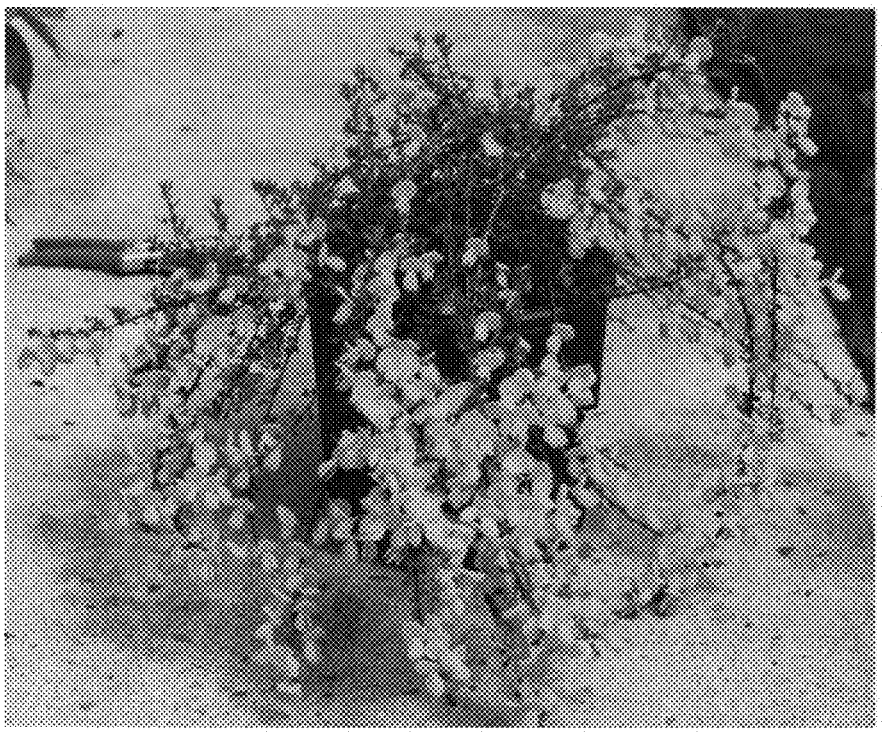

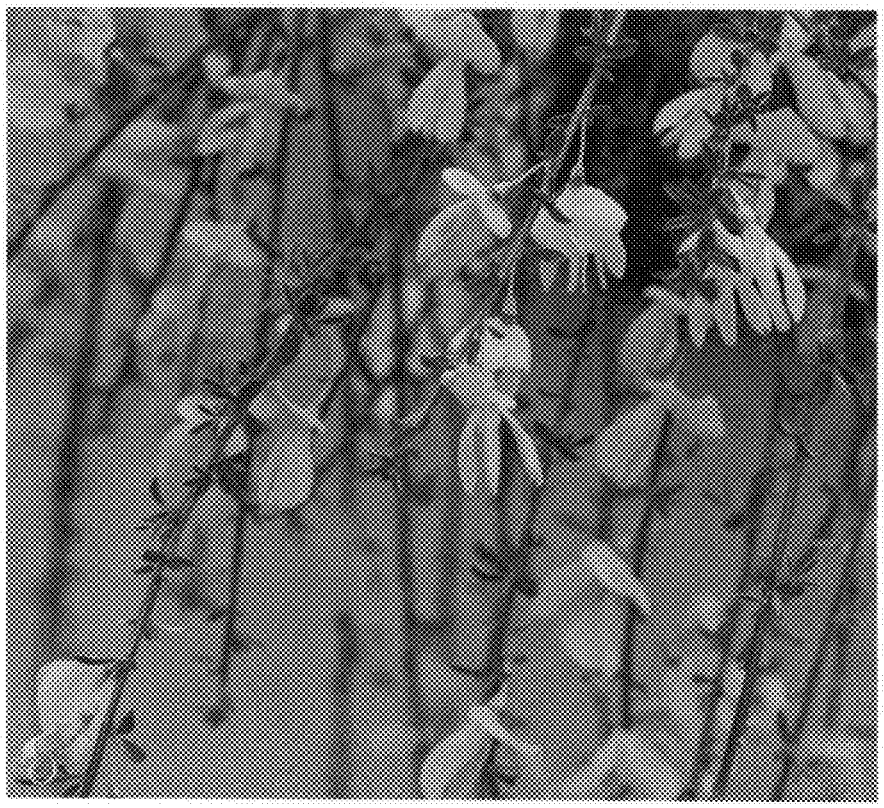

* * * * *